US005614506A

United States Patent [19]
Falk et al.

[11] Patent Number: 5,614,506
[45] Date of Patent: Mar. 25, 1997

[54] USE OF HYALURONIC ACID AND FORMS TO PREVENT ARTERIAL RESTENOSIS

[75] Inventors: Rudolf E. Falk; Samuel S. Asculai, both of Toronto; Eva A. Turley, Winnipeg, all of Canada

[73] Assignee: Hyal Pharmaceutical Corporation, Mississauga, Canada

[21] Appl. No.: 285,764

[22] Filed: Aug. 3, 1994

Related U.S. Application Data

[63] Continuation of Ser. No. 952,095, Sep. 28, 1992, abandoned, which is a continuation-in-part of Ser. No. 675,908, Jul. 3, 1991, Ser. No. 838,674, Feb. 21, 1992, abandoned, and Ser. No. 838,675, Feb. 21, 1992.

[30]  Foreign Application Priority Data

Sep. 25, 1992 [CA] Canada .................................. 2079205-1

[51] Int. Cl.$^6$ .................................................... A61K 31/70
[52] U.S. Cl. ............................................. 514/54; 536/55.1
[58] Field of Search ................................ 536/55.1; 514/54

[56]  References Cited

U.S. PATENT DOCUMENTS

| | | | |
|---|---|---|---|
| 2,583,096 | 1/1952 | Hadidian et al. | 424/497 |
| 3,436,454 | 4/1969 | Nouvel | 424/401 |
| 3,887,703 | 6/1975 | Manoussos et al. | 424/581 |
| 4,141,973 | 2/1979 | Balasz | 536/55.1 |
| 4,272,522 | 6/1981 | Balaza | 424/94.61 |
| 4,582,865 | 4/1986 | Balazs et al. | 524/29 |
| 4,636,524 | 1/1987 | Balazs et al. | 514/781 |
| 4,711,780 | 12/1987 | Fahim | 424/641 |
| 4,716,154 | 12/1987 | Mälson et al. | 514/54 |
| 4,716,224 | 12/1987 | Sakurai et al. | 536/551 |
| 4,725,585 | 2/1988 | Wenge et al. | 514/54 |
| 4,736,024 | 4/1988 | Della Valle et al. | 536/55.3 |
| 4,746,504 | 5/1988 | Nimrod et al. | 514/54 |
| 4,755,544 | 7/1988 | Makino et al. | 524/42 |
| 4,795,741 | 1/1989 | Leshchiner et al. | 514/21 |
| 4,801,619 | 1/1989 | Lindblad | 574/42 |
| 4,808,576 | 2/1989 | Schultz et al. | 514/54 |
| 4,814,176 | 3/1989 | Makino et al. | 424/457 |
| 4,840,941 | 6/1989 | Ueno et al. | 514/59 |
| 4,851,521 | 7/1989 | della Valle et al. | 536/55.1 |
| 4,853,226 | 8/1989 | Machida et al. | 424/426 |
| 4,937,254 | 6/1990 | Sheffield et al. | 424/497 |
| 4,946,870 | 8/1990 | Partain, III et al. | 514/55 |
| 4,957,744 | 9/1990 | della Valle et al. | 424/901 |
| 4,965,353 | 10/1990 | della Valle et al. | 536/55.1 |
| 4,970,298 | 11/1990 | Silver et al. | 530/356 |

FOREIGN PATENT DOCUMENTS

| | | |
|---|---|---|
| 30806/84 | 7/1984 | Australia . |
| 72117/87 | 12/1987 | Australia . |
| 17459/88 | 12/1988 | Australia . |
| 1205031 | 5/1986 | Canada . |
| 1240929 | 8/1988 | Canada . |
| 0138572 | 4/1985 | European Pat. Off. . |
| 0179442 | 4/1986 | European Pat. Off. . |
| 0197718 | 10/1986 | European Pat. Off. . |
| 0208623 | 1/1987 | European Pat. Off. . |
| 0216453 | 4/1987 | European Pat. Off. . |
| 0224987 | 6/1987 | European Pat. Off. . |
| 0240098 | 10/1987 | European Pat. Off. . |
| 0265116 | 4/1988 | European Pat. Off. . |
| 0270317 | 6/1988 | European Pat. Off. . |
| 0285357 | 10/1988 | European Pat. Off. . |
| 0287210 | 10/1988 | European Pat. Off. . |
| 0295092 | 12/1988 | European Pat. Off. . |
| 0296740 | 12/1988 | European Pat. Off. . |
| 0378852 | 7/1990 | European Pat. Off. . |
| 2364373 | 10/1975 | Germany . |
| 57-183707 | 12/1982 | Japan . |
| 61-000017 | 1/1986 | Japan . |
| 61-233622 | 10/1986 | Japan . |
| 63-116678 | 5/1988 | Japan . |
| 1283892 | 8/1972 | United Kingdom . |
| 2099826 | 12/1982 | United Kingdom . |
| WO88/07060 | 9/1988 | WIPO . |
| WO89/07932 | 9/1989 | WIPO . |
| WO91/04058 | 4/1991 | WIPO . |

OTHER PUBLICATIONS

Alaverdyan MI, Ter–Avetisyan AT. Effect of hyaluronidase, hyaluronic acid, and some other substances on postradiational experimental bacteriemai. *Bulletin of Experimental Biology and Medicine* 1967; 64(9): 967–969.

Balaza EA, Band P. Hyaluronic acid: Its structure and use. *Cosmetics & Toiletries.* Polymers in Cosmetics 1984; 99: 65–72.

Balaza EA, Gibbs DA. The rheological properties and biological function of hyaluronic acid. In: *Chemistry and Molecular Biology of the Intercellullar Matrix.* vols. III. New York: Academic Press, 1970. pp. 1241–1253.

Balazs EA, B and P. Hyaluronic acid: Its structure and use. *Cosmetics & Toiletries.* Polymers in Cosmetics 1984; 99: 65–72.

Camber O, Edman P. Gurny R. Influence of sodium hyaluronate on the meiotic effect of pilocarpine in rabbits. *Current Eye Research* 1987; 6(6): 779–784.

Camber O, Lundgren P. Diffusion of some low molecular weight compounds in sodium hyaluronate. *Acta Pharmaceutica Suecica* 1985; 22(6): 315–320.

Chang N–S. Pro–drug and vehicle approaches to improve the therapeutic index of topically applied timolol in the pigmented rabbit. *Dissertation Abstracts International* 1988; 49(2): 367–B.

(List continued on next page.)

*Primary Examiner*—Elli Peselev
*Attorney, Agent, or Firm*—Ivor M. Hughes; Neil H. Hughes

[57]  ABSTRACT

For the prevention of the narrowing of the tubular walls of an animal after the tubular walls have been traumatized, the administration of a therapeutically effective non-toxic amount of hyaluronic acid and/or salts thereof and/or homologues, analogues, derivatives, complexes, esters, fragments, and subunits of hyaluronic acid to the animal to prevent narrowing of the tubular walls.

17 Claims, No Drawings

OTHER PUBLICATIONS

Cravioto RO, Massieu GH, Izquierdo JJ. Effects of precipitated formed by insulin with hyaluronic acid and mucoid from vitreous humor in depressing blood–sugar levels. *Science* 1950; 111: 520–521.

Gieldanowski, Jerzy; Skowronska, Jadwiga Studies on immunosuppressive and anti–inflammatory effect of adriamycin. *Arch. Immunol. Ther. Exp.* (1980); 28 (3): 439–446.

Hassan HG, Akerman B, Ranck H, Lindberg B, Lindquist B. Effects of adjuvants to local anaesthetics on their duration. *Acta Anaesthesiol. Scand.* 1985; 29: 384–388.

Hurd ER Immunosuppressive and anti–inflammatory properties of cyclophosphamide, azathioprine and methotrexate. *Arthritis and Rheumatism* (1973) Jan.–Feb.); 16 (1): 84–88.

Idson B. Polymers in skin cosmetics. *Cosmetics & Toiletries* 1988; 103: 63–68.

Johansson A, Hassan H, Renck H. Effects of adjuvants to local anaesthetics on their duration. *Acta Anaesthesiol. Scand.* 1985; 29: 736–738.

Kalbhen DA. The inhibitory effects of steroidal and non–steroidal antirheumatic drugs on articular cartilage in osteoarthrosis and its counteraction by a biological GAG–peptide complex ("Rumalon"). *Zeitschrift fur Rheumatologie* 1982; 41(5): 340–202–211.

Katsu M., Abe T., Shimada S. Significance and clinical use of non–steroid anti–inflammatory drugs as substitutes for steroids in steroid dependence. *Nippon Rinsho* (1968 Jan. ); 26(1): 89–95.

Kreis H, Chkoff N, Droz D, et al. Nonsteroid anti–inflammatory agents as a substitute treatment for steroids in ATGAM–treated cadaver kidney recipients. *Transplantation* (1984 Feb.); 37(2); 139–145.

McIlwraith W. Current concepts in equine degenerative joint disease. *Journal of the American Veterinary Medical Association* 1982; Feb. 1: 239–250.

Mizushima, Y. Possibility of non–steroid anti–inflammatory drugs as a substitute for seroids–analysis of the present situation and demands for the future. *Nippon Rinsho* (Jan. 1986); 26(1): 61–65.

Nizolek DJH, White KK. Corticosteroid and hyaluronic acid treatmens in equine degenerative joint disease: A review. *The Cornell Veterinarian* 1981; 71(4): 355–375.

Pigman W, et al. Acide hyaluronique et facteurs de perméabilité tissulaire *Bull. Soc. Chim. Biol.* 1963; 45(2–3): 185–202.

Pruett RC, Schepens CL, Constable IJ, Swann DA. Hyaluronic acid vitreous substitute. In: *Vitreous Surgery and Advances in Fundus Diagnosis and Treatment.* Freeman H.M., et al., Editors. Appleton–Century–Crofts, 1977: Chapter 55, pp. 433–444.

Reim M, Teping C. Surgical procedures in the treatment of most severe eye burns. *Acta Ophthalmologica* 1989–Supplementum 192; 67: 47–54.

Rydell NW, Balazs EA. Effect of intra–articular injection of hyaluronic acid on the clinical symptoms of osteoarthritis and on granulation tissue formation. *Clinical Orthopaedics and Related Research* 1971; 80(Oct.): 25–29.

Saba P, Galeone F, Salvadorini F, Guarguaglini M, Ombrato M. Investigation of the Antihyperlipemic activity of an association of clofibrate and extractive mucopolysaccharide complex. *Current Therapeutic Research* 1978: 23(4): 455–463.

Stegman R, Miller D. Use of sodium hyaluronate in severe penetrating ocular trauma. *Acta Ophthalmol.* 1986; 18: 9–13.

Trabucchi E, Foschi D, Marazzi M, Radaelli E, Lucianetti A, Rizzitelli E, Baratti C, et al. Prevention of wound dehiscence in severely obese patients with jejuno–ileal by–pass: The role of hyaluronic acid. *Pharmatherapeutica* 1988; 5(4): 233–239.

Sertoli P, Merello A, Parodi M. L'acido jaluronica, per uso topico, nella cura delle ulcere trofocircolatorie degli arti inferiori. (Comunicazioni). *Giornale Italiano di Dermatologia* 1970; 45(8): 468–471.

Walther, M. The Prevention of Strine Cutis Sistansae During Pregnancy. *Mineva Gynecolgia* (1981) vol. 33: 497–499.

Weirich, E.G., Longauer, J.K., Kirkwood, A.H. Dermatopharmacology of salicylic acid. III. Topical contra–inflammatory effect of salicylic acid and other drugs in animal experiments. *Dermatologica* (1976); 152(2): 87–99.

Sandra Blakeslee, "Solid cores of tumors keeping out best drugs", Jul. 8, 1989 edition of the Globe and Mail; Toronto, Ontario, p. D4.

Pam Harrison, "Toxic drug tamed but still potent" *Ontario Medicine*, vol. 8, No. 16 dated Aug. 21, 1989, p. 1.

*The Merck Index* Eleventh Edition, Centennial Edition, Hyaluronic Acid formulation, pp. 751 and 752.

Alan R. Liss, Inc., Modulation of Immunity in Cancer Patients by Prostaglandin Antagonists, *Immunity to Cancer II* (will follow).

Goodwin, J.S. Prostaglandin E and Cancer Growth Potential for Immunotherapy with Prostaglandin Synthesis Inhibitors, *Augmentive Agents in Cancer Therapy*, Raven Press, New York, (1981)(will follow).

Dr. Samuel Asculai, *Inactivation of Herpes Simplex Viruses by Nonionic Surfactants, Antimicrobial Agents and Chemotherapy*, Apr. 1978, pp. 686–690. (will follow).

The Merck Index, 9th ed, 1976 pp. 110–111 and 656, Nos. 855 and 4845.

USE OF HYALURONIC ACID AND FORMS TO PREVENT ARTERIAL RESTENOSIS

This application is a continuation of application Ser. No. 07/952,095, filed on Apr. 28, 1992, now abandoned, which is a continuation-in-part application of each of U.S. patent application Ser. Nos. 07/675,908, (filed on Jul. 3, 1991), 07/838,674, (filed on Feb. 21, 1992), now abandoned, and 07/838,675, (also filed Feb. 21, 1992), each of which is incorporated herein by reference.

FIELD OF INVENTION

This invention relates to the prevention of the narrowing (stenosis) of tubular walls of an animal after the tubular walls have been traumatized. In one embodiment, this invention relates to the prevention of arterial restenosis after balloon angioplasty.

BACKGROUND OF THE INVENTION

Balloon angioplasty is a widely accepted method of opening blockages in the coronary arteries. However in some patients after successful treatment by balloon angioplasty, arterial restenosis occurs. This time however the narrowing of the inner diameter (ID) of the artery is caused by growth (proliferation) of endothelial cells in the areas of irritation caused by the balloon angioplasty. Thus reblockage occurs not by cholesterol build-up but by build up of endothelial cells on the inner wall of the artery reducing the inner diameter (ID) of the artery leading to an infarct. This narrowing of the inner diameter (ID) of tubular walls or proliferation of cells is not however restricted or limited to the coronary arteries. It can also occur post operatively causing restenosis in for example peripheral vascular systems.

A number of proposals have been made in the prior art to prevent restenosis.

U.S. Pat. No. 5,087,244 (Wolinsky et al.) purports to teach the use of a catheter having an inelastic balloon at one end thereof, where the balloon has minute perforations and contains a concentrated heparin solution which will be released through the perforations contacting an area of the artery after angioplasty to prevent restenosis.

U.S. Pat. No. 5,116,864 (Hathaway et al.) purports to teach the prevention of restenosis in peripheral or cardiac vascular systems after vascular recanalisation by systemic administration of photo activatable psoralen to give serum psoralen levels which inhibit smooth muscle cell growth.

U.S. Pat. No. 5,092,841 (Spears, J. R.) purports to teach the treatment of an arterial wall injured during angioplasty by delivering bio-protective material between the wall and the angioplasty catheter so that the bio-protective material is entrapped and permeates into the tissues and vessels of the arterial wall during opposition of the angioplasty catheter.

EP 356275-A (Petitou et al.) purports to teach the use of new o-acylated glycosamino-glycan derivatives in the inhibition of post-operative restenosis.

Berk., B. C. et al in the J. Am. Coll. Cardiol. dated 1991 Vol. 17 #6 Supplement B, pp 111B–117B purports to discuss the pharmacologic roles of heparin and glucocorticoids to prevent restenosis after coronary angioplasty.

WO 9209561 (Itoh et al.) purports to teach the use of new ACAT inhibiting amide derivatives in treatment of restenosis after percutaneous transluminal coronary angioplasty.

WO 9208472 (Scarborough et al.) purports to teach the use of platelet antiadhesive peptide(s) obtained from snake venom for the prevention of restenosis following angioplasty.

WO 9207852 (Bovy et al.) purports to teach the use of certain biphenylalkyl xanthine derivatives to prevent post-angioplasty restenosis.

WO 9205782 (Pill, J.) purports to teach the use of thromboxane-A2-receptor antagonists (I) in the preparation of medicaments for inhibition of proliferative developments in obstructive vascular disorders ie. arterial restenosis.

WO 9118639 (GAj et al.) purports to teach the inhibition of stenosis after balloon angioplasty, by the administration of fibronectin by continuous or bolus infusion, or by direct infusion into the stenotic region via the angioplasty catheter.

CA 2,042,159 laid open application (Ondetti, et al.) purports to teach the use of ACE inhibitor (via the oral or parenteral route) for preventing or reducing the risk of restenosis following angioplasty.

U.S. Pat. No. 4,929,602 (Harker, et al.) purports to teach a method of inhibiting arterial restenosis by administration of D-phenyl alanyl-prolyl-arginylbalomethyl ketone peptide derivative or a hydrolalin acid addition thereof.

U.S. Pat. No. 4,820,732 (Shell, et al.) purports to teach a composition containing a prostaglandin compound for the reduction of restenosis and abrupt stenosis.

Applicant is also aware of a company Glycomed developing a fragment of Heparin that prevents arterial restenosis after balloon angioplasty.

In the basic research efforts in the latter '70s and the early 80's, there existed considerable confusion as to what role immunotherapy should take in cancer. Activation or "hyping" of macrophages was thought to be important. However, in an examination by Romans and Falk of peritoneal macrophages obtained from patients with neoplastic disease, there was definite evidence that these macrophages were already activated yet were co-existing with cancer cells and not causing their destruction.

It has been shown by several independent investigators that the malfunction of macrophages or the putitive block is due to excessive prostaglandin and that this can be altered in tissue culture by corticosteroids, ASA, and the non-steroidal anti-inflammatory drugs, i.e. indomethacin, and naproxen (Naprosyn™). Again, in animal tumors it was repeatedly demonstrated that these substances could alter the response to neoplastic cells and that various combinations of these substances employed with immune enhancing agents could produce very credible success in eliminating experimental tumors. Lala and co-workers combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastrointestinal, neurological, and other areas. Thus, the basis of the present approach is that under general circumstances the use of these agents in human disease, in sufficient amounts, the drug will penetrate to any pathological tissue to alter therapeutically local prostaglandin production. While intravenous preparations exist of Indomethacin and now of other agents, the data is overwhelming, as is our own experience, that using these drugs alone produces prohibitive side effects in human subjects. Therefore only insufficient amounts can be brought into the body to effect more than occasional responses in neoplasm.

However the majority of the evidence is present to indicate and therefore it can be postulated that the basis for neoplastic development and how the initial cell "sneaks by" the immune surveillance mechanism relates to its production of prostaglandin. One need postulate only one mutation to alter the amount of prostaglandin synthesis produced by cells when they become "malignant" to establish a mechanism of blocking out the initial cell in any immune reaction, i.e. the macrophage. It therefore became essential to develop a combination of NSAIDS for clinical use to produce a major improvement in response to neoplastic disease and other conditions where excessive prostaglandin synthesis represents the basis of the pathogenesis of this disease state, i.e. arthritis, and various others of the so-called connective tissue inflammatory disorders and/or auto-aggressive diseases.

See also:
1. Modulation of Immunity in Cancer Patients by Prostaglandin Antagonists, *Immunity to Cancer II*, Alan R. Liss, Inc.; and
2. Goodwin, J. S. (1981) Prostaglandin E and Cancer Growth Potential for Immunotherapy with Prostaglandin Synthesis Inhibitors, *Augmentive Agents in Cancer Therapy*, Raven Press, New York.

It is therefore an object of this invention to provide a method of treatment and formulations and pharmaceutical compositions for preventing arterial restenosis after balloon angioplasty when endothelial cell proliferation occurs on the inner arterial wall caused by irritation to the cells by balloon angioplasty.

It is a further object of the invention to provide such treatment using hyaluronic acid which is safe and essentially non-toxic.

Further and other objects of the invention will be realized by persons skilled in the art from the following summary of the invention and discussion with respect thereto.

SUMMARY OF THE INVENTION

Applicants believe that forms of hyaluronic acid (especially hyaluronic acid and salts thereof) will prevent stenosis of the inner diameter (ID) of irritated tubular walls and particularly prevent restenosis of the arterial walls by for example the proliferation of endothelial cells as a result of irritation arising from balloon angioplasty. The forms of hyaluronic acid (for example hyaluronic acid and salts of hyaluronic acid) can be administered intravenously or by injection (in the case of direct injection of small amounts) in effective amounts of about 10 mg/70 kg person to in excess of 3000 mg/70 kg person.

Therefore according to one aspect of the invention, there is provided a process for the prevention of the narrowing of the tubular walls of an animal after the tubular walls have been traumatized (for example wherein the tubular walls are arteries which have been subjected to balloon angioplasty) the process comprising the administration of a therapeutically effective non-toxic amount of hyaluronic acid and/or salts thereof and/or homologues, analogues, derivatives, complexes, esters, fragments and subunits of hyaluronic acid to the animal to prevent narrowing of the tubular walls. Preferably the form of hyaluronic acid is hyaluronic acid and salts thereof. The amount of the form of hyaluronic acid administered is preferably between about 10 mg/70 kg person and about 3000 mg/70 kg person.

Thus according to another aspect of the invention, a process is provided for the prevention of arterial restenosis after balloon angioplasty in a human, the process comprising the administration of a therapeutically effective non-toxic amount of hyaluronic acid and/or salts thereof and/or homologues, analogues, derivatives, complexes, esters, fragments, and subunits of hyaluronic acid to the human to prevent arterial restenosis. Once again preferably the form of hyaluronic acid is hyaluronic acid and salts thereof and preferably the amount of the form of hyaluronic acid administered is between about 10 mg/70 kg person and about 3000 mg/70 kg person.

The compositions are preferably administered intravenously in a liquid form and include suitable diluents or other adjuvants as required for administration. With respect to small amounts to be administered, they may be administered by injection preferably at or proximate the site to be treated.

A therapeutically effective amount of a non-steroidal anti-inflammatory drug (NSAID) for enhancing the effect of the form of hyaluronic acid administered in the prevention of the narrowing of the tubular walls may be administered with the form of the hyaluronic acid. The addition of the nonsteroidal anti-inflammatory agent will enhance the activity of the hyaluronic acid in preventing the narrowing of the tubular walls for example enhancing the arterial restenosis prevention effect of the administered hyaluronic acid and/or salts thereof. The NSAID may be an NSAID suitable for the purposes and which may comprise Diclofenac, Indomethacin (solubilized in N-Methyl Glucamine), Piroxicam, the tromethamine salt of Ketorolac, acetylsalicylic acid, Naproxen and the like. The amounts of NSAID may be appropriate accepted doses preferably administered to patients. In some cases dose amounts up to 10 mg of the NSAID/kg of body weight (for example 1–2 mg of NSAID/kg of body weight) are suitable. With Diclofenac much larger amounts are appropriate. Where greater than normal amounts of NSAIDS are used, in order to reduce side effects caused by excess NSAID administration, greater than about 200 mg of the form of Hyaluronic Acid (HA) per 70 kg person may be administered to reduce and eliminate the side effects such as gastro-intestinal distress, neurological abnormalities, depression, etc.

A therapeutically effective amount of Vitamin C may also be added to the composition to enhance the effect of the Hyaluronic Acid administered. Such amount may be up to 50 grams–100 grams in a dosage as Vitamin C is soluble and is excreted by the kidney although much lower amounts are normally used. Preferably the composition comprises a form of hyaluronic acid, specifically preferred hyaluronic acid and/or salts thereof, an NSAID and Vitamin C for administration for the prevention of the narrowing of the tubular walls (for example the prevention of arterial restenosis after balloon angioplasty.

Thus according to another aspect of the invention, the use of a pharmaceutical composition for the prevention of the narrowing of the tubular walls of an animal after the tubular walls have been traumatized is provided, the use being of a pharmaceutical composition comprising a therapeutically effective non-toxic amount of hyaluronic acid and/or salts thereof and/or homologues, analogues, derivatives, complexes, esters, fragments, and subunits of hyaluronic acid in association with a suitable diluent or pharmaceutically acceptable carrier or other adjuvants to prevent narrowing of the tubular walls. Preferably the form of hyaluronic acid is hyaluronic acid and salts thereof.

According to another aspect of the invention, the use of a pharmaceutical composition for the prevention of arterial restenosis after balloon angioplasty in a human is provided, the use being of a pharmaceutical composition comprising a therapeutically effective non-toxic amount of hyaluronic acid and/or salts and/or homologues, analogues, derivatives, complexes, esters, fragments, and subunits of hyaluronic acid in association with a suitable diluent, pharmaceutically acceptable carrier or other adjuvants to prevent arterial restenosis preferably the form of hyaluronic acid is selected from hyaluronic acid and salts thereof and the amount of the form of hyaluronic acid is between about 10 mg/70 kg person and about 3000 mg/70 kg person.

In one embodiment the form of the pharmaceutical composition is for intravenous administration.

According to still another aspect of the invention, the pharmaceutical composition comprises a therapeutically effective amount of non-steroidal anti-inflammatory drug (NSAID) for example Diclofenac, Indomethacin (solubilized in N-Methyl Glucamine), Piroxicam, the tromethamine salt of Ketorolac, acetylsalicylic acid and the like for enhancing the effect of the form of hyaluronic acid in the prevention of the narrowing of the tubular walls.

Thus according to another aspect of the invention, the use of a pharmaceutical composition for the prevention of arterial restenosis after balloon angioplasty is provided, the use being of a pharmaceutical composition comprising a therapeutically effective non-toxic amount of hyaluronic acid and/or salts thereof in association with a suitable diluent or pharmaceutically acceptable carrier or other adjuvants to prevent arterial restenosis (by administration for example intravenously of the composition). In some embodiments the amount of the hyaluronic acid and/or salts thereof is between about 10 mg/70 kg person and about 3000 mg/70 kg person. The composition may further comprise a therapeutically effective amount of a non-steroidal anti-inflammatory drug (NSAID) for enhancing the arterial restenosis prevention effect of the administered hyaluronic acid and/or salts thereof administered. The NSAID may be at accepted appropriate doses depending on the NSAID for example up to about 10 mg/70 kg of body weight (for example 1–2 mg of NSAID/kg of body weight). The appropriate dose for Diclofenac is much greater. Where it is desired to use a dose excess of NSAID, the amount of hyaluronic acid and salts thereof preferably exceeds about 200 mg/70 kg person.

The composition may further comprise a therapeutically effective amount of Vitamin C for enhancing the effects of the form of hyaluronic acid to prevent narrowing of the tubular walls. The Vitamin C may be used in large amounts (for example even 50–100 grams) although much smaller amounts are suitable.

According to another aspect of the invention the use of:
- an effective non-toxic amount of hyaluronic acid and/or salts thereof and/or homologues, analogues, derivatives, complexes, esters, fragments, and subunits of hyaluronic acid,
- in the manufacture of a pharmaceutical composition is provided for preventing the narrowing of the tubular walls of an animal after the tubular walls have been traumatized, the use being characterized by a therapeutically effective non-toxic amount of hyaluronic acid and/or salts thereof and/or homologues, analogues, derivatives, complexes, esters, fragments, and subunits of hyaluronic acid being incorporated into the pharmaceutical composition and being sufficient and effective to prevent the narrowing of the tubular walls which were traumatized as for example the arteries being damaged after balloon angioplasty. Preferably the form of hyaluronic acid is hyaluronic acid and/or salts thereof and the composition is in a liquid form. Preferably, the form of hyaluronic acid is utilized at a dose between about 10 mg to about 3000 mg/70 kg person and more preferably the form of hyaluronic acid is utilized at a dose greater than 200 mg/70 kg person.

In one embodiment the pharmaceutical composition is for prevention of arterial restenosis after balloon angioplasty in humans.

According to another aspect of the invention, the use of;
(1) hyaluronic acid and/or salts thereof and/or homologues, analogues, derivatives, complexes, esters, fragments, and subunits of hyaluronic acid, and
(2) an agent selected from a non-steroidal anti-inflammatory drug (NSAID) and Vitamin C and combinations thereof is provided in the manufacture of a pharmaceutical composition (including diluents, adjuvants and other carriers) for preventing the narrowing of the tubular walls of an animal after the tubular walls have been traumatized wherein a therapeutically effective amount of the hyaluronic acid and/or salts thereof and/or homologues, analogues, derivatives, complexes, esters, fragments, and subunits of hyaluronic acid is administered to humans together with a therapeutically effective amount of the agent (2), the use being characterized in that the amount of component (1) is an effective amount to prevent the narrowing of the tubular walls of the animal and component (2) enhances the effect of component (1) in the prevention of the narrowing of the tubular walls.

Preferably component (2) is hyaluronic acid and/or salts thereof and the composition is in a liquid form (for example for intravenous use or injection). Preferably component (1) is utilized at a dose between about 10 mg to about 3000 mg/70 kg person and more preferably component (1) is utilized at a dose greater than 200 mg/70 kg person.

Component 2 is utilized at amounts effective to enhance the effect of Component 1. Vitamin C may be utilized in amounts up to 50–100 grams per dose although much smaller amounts are more desirable. The NSAID can be administered in normally acceptable dose amounts depending on the NSAID. With some NSAIDS the amounts are 1–2 mg of NSAID per Kg of body weight, in others up to about 10 mg per kg bodyweight and in others such as Diclofenac, much larger amounts. Where the NSAID is used in dose excesses (greater amounts than the normally acceptable dose amounts, the amount of the form of hyaluronic acid exceeds about 200 mg per 70 kg person. Suitable NSAIDS are Diclofenac, Piroxicam, Indomethacin (solubilized in N-methyl glucamine), acetylsalicylic acid, ± tromethamine salt of Ketorolac, naproxen and the like.

According to another aspect of the invention a pharmaceutical composition is provided comprising (together with diluents as required) an effective non-toxic amount of hyaluronic acid and/or salts thereof and/or homologues, analogues, derivatives, complexes, esters, fragments, and subunits of hyaluronic acid, for preventing the narrowing of the tubular walls of an animal after the tubular walls have been traumatized, the composition being characterized by an effective non-toxic amount of hyaluronic acid and/or salts thereof and/or homologues, analogues, derivatives, complexes, esters, fragments, and subunits of hyaluronic acid being incorporated into the pharmaceutical composition to prevent the narrowing of the tubular walls. Preferably the form of hyaluronic acid is hyaluronic acid and/or salts thereof and preferably the composition is in a liquid form (for example an intraveneous (I.V.) form in an I.V. bag with diluents and pharmaceutically acceptable carriers and adjuvants). The form of hyaluronic acid may be utilized at doses between about 10 mg to about 3000 mg/70 kg person and preferably the form of hyaluronic acid is utilized at a dose greater than 200 mg/70 kg person (especially where dosage excesses of NSAIDS are employed). In one embodiment the pharmaceutical composition is for prevention of arterial restenosis after balloon angioplasty in humans.

According to another aspect of the invention, a pharmaceutical composition is provided comprising (together with diluents, adjuvants and other pharmaceutically acceptable carriers as and if desired);

(1) hyaluronic acid and/or salts thereof and/or homologues, analogues, derivatives, complexes, esters, fragments, and subunits of hyaluronic acid, and (2) an agent selected from a non-steroidal anti-inflammatory drug and Vitamin C and combinations thereof for preventing the narrowing of the tubular walls of an animal after the tubular walls have been traumatized, the composition being characterized by an effective non-toxic amount of hyaluronic acid and/or salts thereof and/or homologues, analogues, derivatives, complexes, esters, fragments, and subunits of hyaluronic acid being incorporated into the composition together with a therapeutically effective amount of the agent (2), to prevent tubular wall narrowing, the composition being characterized that the amount of component (1) is an effective amount to prevent the narrowing of the tubular walls of the animal and the amount of component (2) enhances the effect of component (1) in the prevention of the narrowing of the tubular walls. Preferably component (1) is hyaluronic acid and/or salts thereof and preferably in a liquid dosage form, for example in an Intravenous form (I.V. Bag). In some embodiments component (1) may be utilized at a dose between about 10 mg to about 3000 mg/70 kg person. Preferably component (1) is utilized at a dose greater than 200 mg/70 kg person where dose excesses of the NSAID of component (2) are utilized. In one embodiment the pharmaceutical composition is for prevention of arterial restenosis after balloon angioplasty in humans.

Component 2 is utilized at amounts effective to enhance the effect of Component 1. Vitamin C may be utilized in amounts up to 50–100 grams per dose. The NSAID can be administered in appropriate dose amounts depending on the NSAID and if given in excess amounts the amount of the form of hyaluronic acid preferably exceeds about 200 mg per 70 kg person. Suitable NSAIDS are Diclofenac, Piroxicam, Indomethacin (solubilized in N-methyl glucamine), acetylsalicylic acid, ± tromethamine salt of Ketorolac, naproxen and the like.

When the composition comprises an agent selected from NSAID and Vitamin C and combinations thereof, Applicants postulate that the hyaluronic acid and/or salts thereof and/or the homologues, analogues, derivatives, complexes, esters, fragments, and/or sub units of hyaluronic acid facilitate the transport of the agent to the site of irritation to enable the agent to penetrate the cells (in the artery, endothelial cells) which together will help prevent for example arterial restenosis.

By way of example and to illustrate the facilitation of the delivery or transport of a chemical to a site in a mammal, when ethyl alcohol is injected directly into a cancer tumor, and sonographic (ultrasound) assessment is made, it is not dispersed throughout the tumor. When the ethyl alcohol to be administered into a tumor is carried by hyaluronic acid and/or salts thereof, sonographic assessment of the tumor, demonstrates the dispersion of the ethyl alcohol throughout the tumor.

While Applicants postulate that the hyaluronic acid facilitates the transport and delivery, Applicants' invention may be used as described irrespective of the actual method of operation of the hyaluronic acid and/or salts thereof and/or the homologues, analogues, derivatives, complexes, esters, fragments and sub units of hyaluronic acid with the NSAID and Vitamin C.

The combination of hyaluronic acid and salts thereof and other forms with different chemicals and drugs (Vitamin C, and NSAIDS) alters their distribution and performance in the human body and produces an unusual targeting for underperfused tissue and/or pathological tissue. In this regard the use of ascorbic acid (Vitamin C) as a free radical scavenger (50 gm daily–1000 times the daily dose in therapeutic purposes as a Vitamin) administered intravenously with 300–500 mg of hyaluronic acid (sodium hyaluronate) immediately relieves bone pain and muscle pain and reduces inflammation in cancer patients. The hyaluronic acid enhances the anti-neoplastic activity and effect of the ascorbic acid. It is thought that this enhanced activity eliminates the free radicals by acting as a free radical scavenger. In any event the patients feel better. This is also demonstrated with furosemide and hyaluronic acid where the activity of furosemide is enhanced only minimally when administered with hyaluronic acid to a "normal" subject but the activity is enhanced significantly when administered to a patient whose kidney is underperfused or malfunctioning due to insufficient intra-vascular volume.

A similar situation occurs with the NSAIDS. As a major amount of soluble indomethacin is required, the chemical product was solubilized using n-methyl glucamine at a dilution of 5 mg/ml of n-methyl glucamine (NMG). This substance is then passed through a 22 micron Milipore filter to produce sterility. This material is non-toxic at 16 fold the therapeutic dose in animals and for this reason was considered appropriate to be used in human conditions. Thus, Indocid™ solubilized in NMG is administered to human patients either into a tumor intraperitoneally, intrapleurally, or intravascularly at a varying dose up to 10 mg/kg where each dose of indomethacin is combined with 200–1000 mg of hyaluronic acid (for example "LifeCore™" hyaluronic acid [sodium hyaluronate]) diluted in the original solution of indomethacin and NMG with for example the "LifeCore™" hyaluronic acid. This produces an appropriate mixture and can be administered safely by any of the routes. [Similar clinical studies have been done with hyaluronic acid prepared by other methods, i.e. extraction. The extracted material is satisfactory to use for intratumor, intraperitoneal or intrapleural use with this substance.]

Thus when an NSAID for example indomethacin (dissolved in n-methyl glucamine) or other NSAID is administered with greater than 200 mg hyaluronic acid for 1–2 mg/kg body weight of the NSAID (in one instance indomethacin and NMG), no major toxic side effects occur such as gastro-intestinal distress, neurological abnormalities, depression, etc., even at elevated amounts of indomethacin (if necessary). If the amount of hyaluronic acid is decreased below that amount, the usual side effects may begin to reoccur. In addition, the responses that have been observed are superior when the NSAID (for example Indocid™) is combined with hyaluronic acid demonstrating clearly that the combination is now "targeting" to the pathological tissue even when administered by the systemic intravenous route. Thus, it has been observed that patients with neoplastic diseases when receiving in addition to other chemicals (for example ascorbic acid [Vitamin C], phloretin and anti-cancer drugs), 50–200 mg NSAID—hyaluronic acid (sodium hyaluronate) (for example indomethacin and hyaluronic acid) experience dramatic relief of pain immediately. This is followed within a short period of time by a resolution and resorbtion of neoplastic lesions with an improvement of pulmonary, and liver function if there is tumor present in these organs. Thus the dead tumor material and the debris and tumor toxins appear to be better eliminated by the body through the action of the macrophages whose activity is enhanced by the addition of the NSAID (or a steroidal anti-inflammatory drug) administered with hyaluronic acid (or salt or other form thereof). Thus Applicants believe that the addition of the NSAID for example with hyaluronic acid (sodium hyaluronate) deblocks the macrophages by preventing enzymatic production of prostaglandin synthetase which blocks macrophage functioning. Thus the hyaluronic acid (and salt and other forms) not only enhance the activity of the NSAID but also reduce any side effects and toxicity that is associated with the use of the prostaglandin synthesis inhibitors.

The hyaluronic acid and salts thereof may be utilized at varying doses −10 to 1000 mg/70 kg person. As there is no toxicity, the hyaluronic acid can obviously be administered in a dose excess (for example 3000 mg/70 kg individual) without any adverse effects.

One form of hyaluronic acid and/or salts thereof (for example sodium salt) and homologues, analogues, derivatives, complexes, esters, fragments, and sub units of hyaluronic acid, preferably hyaluronic acid and salts and thereof suitable for use with Applicant's invention is a fraction supplied by Sterivet Laboratories Limited (now Hyal Pharmaceutical Corporation). One such fraction is a 15 ml vial of Sodium hyaluronate 20 mg/ml (300 mg/vial—Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and sub units of hyaluronic acid, preferably hyaluronic acid and salts thereof may comprise hyaluronic acid and/or salts thereof having the following characteristics:

a purified, substantially pyrogen-free fraction of hyaluronic acid obtained from a natural source having at least one characteristic selected from the group consisting of the following:

i) a molecular weight within the range of 150,000–225,000;

ii) less than about 1.25% sulphated mucopoly-saccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25; and xii) a pH within the range of 7.3–7.9. Preferably the hyaluronic acid is mixed with water and the fraction of hyaluronic acid fraction has a mean average molecular weight within the range of 150,000–225,000. More preferably the fraction of hyaluronic acid comprises at least one characteristic selected from the group consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

x) a UV extinction coefficient at 257 nm of less than about 0.23;

xi) a UV extinction coefficient at 280 nm of less than 0.19; and xii) a pH within the range of 7.5–7.7

Other forms of hyaluronic acid and/or its salts, and homologues, derivatives, complexes, esters, fragments and sub units of hyaluronic acid may be chosen from other suppliers, for example those described in prior art documents. In addition Applicants propose the use of sodium hyaluronate produced and supplied by LifeCore™ Biomedical, Inc. having the following specifications

| Characteristics | Specification |
| --- | --- |
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, maximum ppm | |

| As | Cd | Cr | Co | Cu | Fe | Pb | Hg | Ni |
| --- | --- | --- | --- | --- | --- | --- | --- | --- |
| 2.0 | 5.0 | 5.0 | 10.0 | 10.0 | 25.0 | 10.0 | 10.0 | 5.0 |

| Microbial Bioburden | None observed |
| --- | --- |
| Endotoxin | <0.07 EU/mg NaHy |
| Biological Safety Testing | Passes Rabbit Ocular Toxicity Test |

The following references teach hyaluronic acid, sources thereof and processes of the manufacture and recovery thereof.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 cm³/g., and preferably greater than about 2000 cm³/g.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11\times10^3$ degree $-cm^2$/mole (of disaccharide) measured at 220 nanometers;

(f) no significant cellular infiltration of the vitreous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

Where high molecular weight hyaluronic acid (or salts or other forms thereof) is used, it must be diluted to permit administration and ensure no intramuscular coagulation.

One formulation of Ascorbic Acid (Vitamin C) injection USP is manufactured by Steris Laboratories, Inc., Phoenix, Ariz., 85043 U.S.A. and comprises 22 mg/ml (equivalent to sodium ascorbate 250 mg/ml) in 30 ml, 50 ml, or 100 ml individual containers, 30 ml size being preferred.

As many changes can be made to the invention without departing from the scope of the invention, it is intended that all material contained herein by interpreted as illustrative of the invention and not in a limiting sense.

The embodiments of the invention in which an exclusive property or privilege is claimed are as follows:

1. A method of preventing the narrowing of the tubular walls of an animal after the tubular walls have been traumatized, said method comprising the administration of a therapeutically effective non-toxic amount of a form of hyaluronic acid to the animal in need thereof, the form of hyaluronic acid selected from the group consisting of hyaluronic acid, pharmaceutically acceptable salts thereof, and combinations thereof.

2. The method of claim 1, wherein the form of hyaluronic acid is sodium hyaluronate having a molecular weight less than 750,000 daltons.

3. The method of claim 1, wherein the tubular walls are arteries which have been subjected to balloon angioplasty.

4. The method of claim 2, wherein the amount of sodium hyaluronate administered is between about 10 mg/70 kg person and about 3000 mg/70 kg person.

5. A method of preventing arterial restenosis after balloon angioplasty in a human, said method comprising the administration of a therapeutically effective non-toxic amount of a form of hyaluronic acid to the human in need thereof, the form of hyaluronic acid selected from the group consisting of hyaluronic acid, pharmaceutically acceptable salts thereof, and combinations thereof.

6. The method of claim 5, wherein the form of hyaluronic acid is sodium hyaluronate having a molecular weight less than 750,000 daltons.

7. The method of claim 6, wherein the amount of the sodium hyaluronate administered is between about 10 mg/70 kg person and about 3000 mg/70 kg person.

8. The method of claim 1, 2 or 3 wherein the form of hyaluronic acid is administered intravenously.

9. The method of claim 5 or 6 wherein the form of hyaluronic acid is administered intravenously.

10. The method of claim 1, 2 or 3 further comprising administering a therapeutically effective amount of a non-steroidal anti-inflammatory drug with the form of hyaluronic acid for enhancing the effect of the form of hyaluronic acid administered in the prevention of the narrowing of the tubular walls.

11. The method of claim 5 or 6 further comprising administering an effective amount of a non-steroidal anti-inflammatory drug with the form of hyaluronic acid for enhancing the effect of the form of hyaluronic acid administered in the prevention of the arterial restenosis.

12. A method of preventing arterial restenosis after balloon angioplasty in a human, said method comprising the administration of a therapeutically effective non-toxic amount of a form of hyaluronic acid to the human in need thereof, selected from the group consisting of hyaluronic acid, pharmaceutically acceptable salts thereof and combinations thereof having a molecular weight less than 750,000 daltons.

13. The method of claim 12, wherein the amount of the form of hyaluronic acid administered is between about 10 mg/70 kg person and about 3000 mg/70 kg person.

14. The method of claim 12 further comprising administering a therapeutically effective amount of an agent selected from the group consisting of a non-steroidal anti-inflammatory drug and Vitamin C and combinations thereof with the form of hyaluronic acid for enhancing the arterial restenosis prevention effect of the administered form of hyaluronic acid.

15. The method of claim 12 further comprising administering an agent selected from the group consisting of a non-steroidal anti-inflammatory drug and Vitamin C and combinations thereof with the form of hyaluronic acid for enhancing the arterial restenosis prevention effect of the form of hyaluronic acid administered, the non-steroidal anti-inflammatory drug being selected in such amount to be effective in enhancing the arterial restenosis prevention effect of the administered form of hyaluronic acid.

16. The method of claim 14 wherein the amount of the non-steroidal anti-inflammatory drug is a dose excess of the non-steroidal anti-inflammatory drug and the amount of hyaluronic acid and salts thereof exceeds about 200 mg/70 kg person.

17. The method of claim 15 wherein the amount of the NSAID is a dose excess of the non-steroidal anti-inflammatory drug and the amount of the form of hyaluronic acid exceeds about 200 mg/70 kg person.

* * * * *